US00PP33392P2

(12) United States Plant Patent
Van Swieten

(10) Patent No.: US PP33,392 P2
(45) Date of Patent: Aug. 24, 2021

(54) ***PHALAENOPSIS* ORCHID PLANT NAMED 'PHALHODIJ'**

(50) Latin Name: ***Phalaenopsis* hybrid**
Varietal Denomination: PHALHODIJ

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,112

(22) Filed: Mar. 10, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALHODIJ', particularly characterized by large, white, dotted flowers with purplish-pink lips, a flat flower shape in lateral view, an apical lobe of the lip that is slightly folded upwards, and is propagated by meristem tissue culture, is disclosed.

3 Drawing Sheets

Genus and species: *Phalaenopsis* hybrid.
Variety denomination: 'PHALHODIJ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHODIJ'.

The new *Phalaenopsis* plant is a product of a planned breeding program conducted by the inventor in Bleiswijk, the Netherlands. The objective of this breeding program was to create a new *Phalaenopsis* plant with attractive, large, white, dotted flowers with purplish-pink lips, suitable for potted plant production.

The new *Phalaenopsis* plant 'PHALHODIJ' is a result of cross-pollination made by the inventor in December 2010 in Bleiswijk, the Netherlands, of the proprietary female, or seed parent, *Phalaenopsis* hybrid '27517-04' (unpatented) with the proprietary male, or pollen parent, *Phalaenopsis* hybrid '30031-01' (unpatented).

The new *Phalaenopsis* was selected by the inventor as a single plant within the progeny of the stated cross-pollination in a controlled greenhouse in Bleiswijk, the Netherlands, in January 2014. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 26, 2018 (Application no. 2018/1205), by Applicant who obtained the subject matter disclosed directly from the inventor. 'PHALHODIJ' has not been made publicly available or sold anywhere in the world prior to the effective filing date of this application with the exception of sales or disclosures made one year or less before the effective filing date of this claimed invention by Applicant who obtained 'PHALHODIJ' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHODIJ' as a new and distinct variety of *Phalaenopsis* plant:

1) Large, white, dotted flowers with purplish-pink lips;
2) Flower shape in lateral view is flat; and
3) Apical lobe of the lip is slightly folded upwards.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in January 2021. Colors in the photographs may differ from the color values cited in the detailed botanical description, which accurately describe the actual colors of the new variety.

DESCRIPTION OF THE NEW VARIETY

Figure 1:
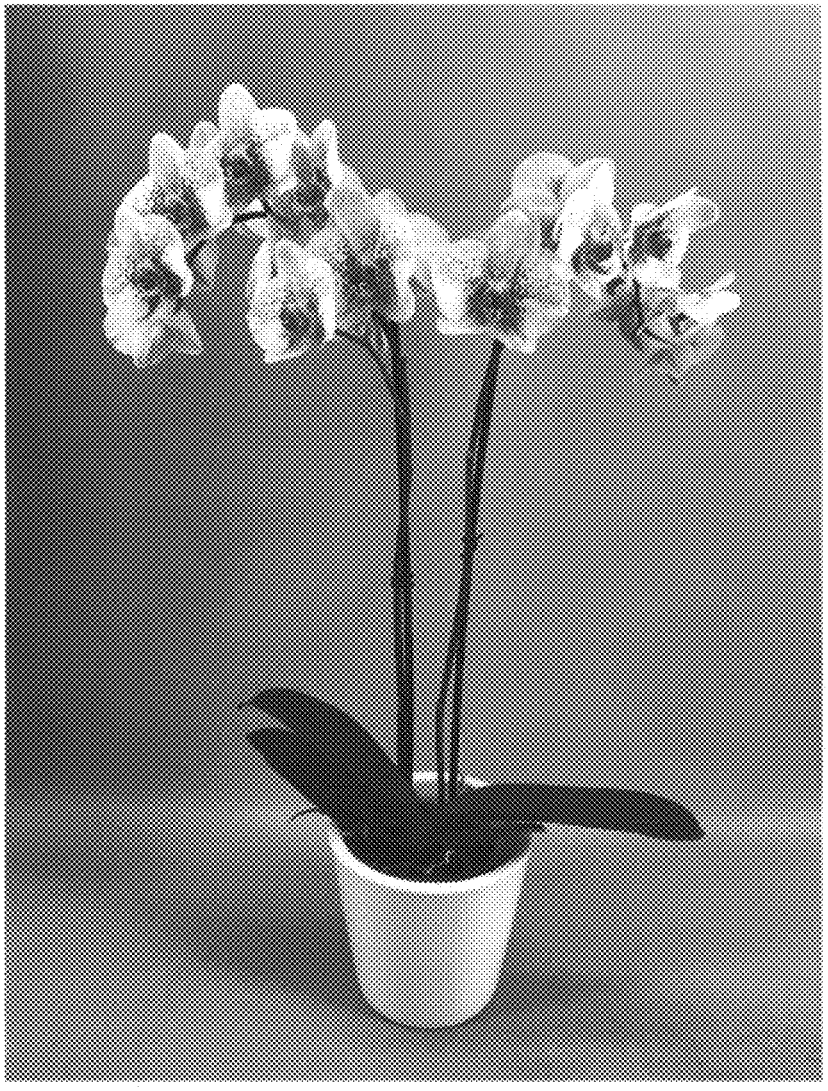
FIG. 1 shows the overall plant habit, including blooms and foliage of 'PHALHODIJ'.
Figure 2:
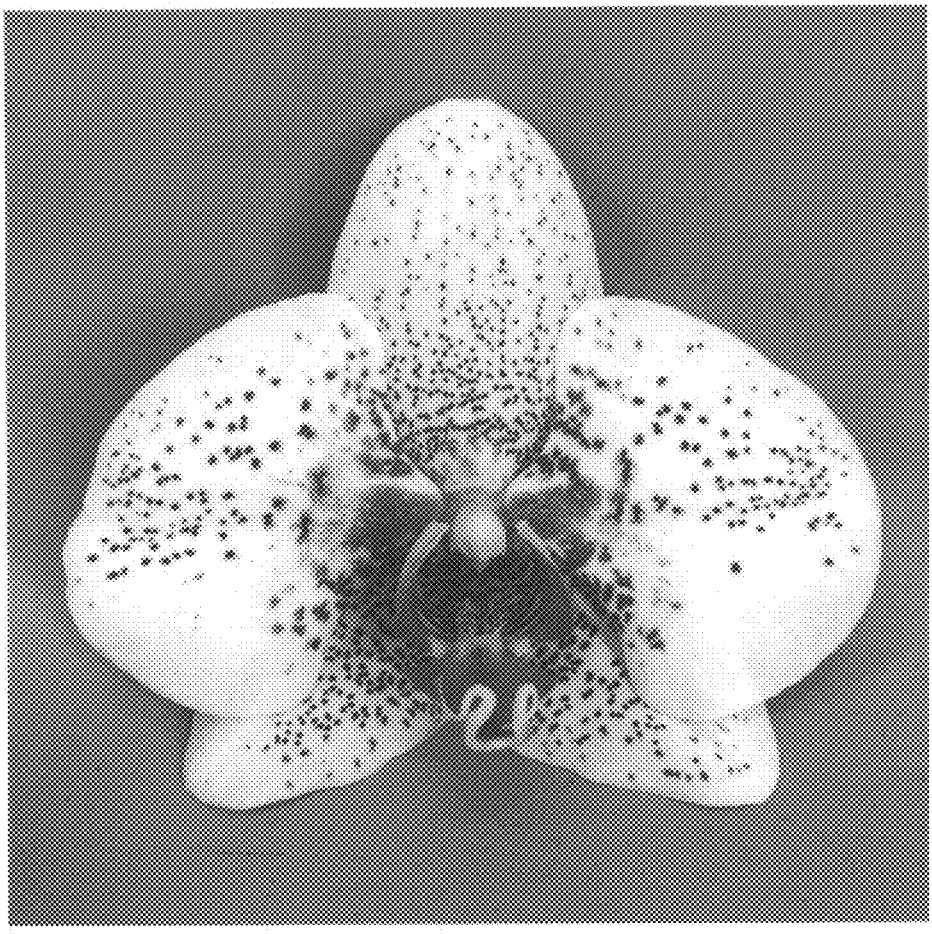
FIG. 2 shows a close-up of a flower of 'PHALHODIJ'.
Figure 3:
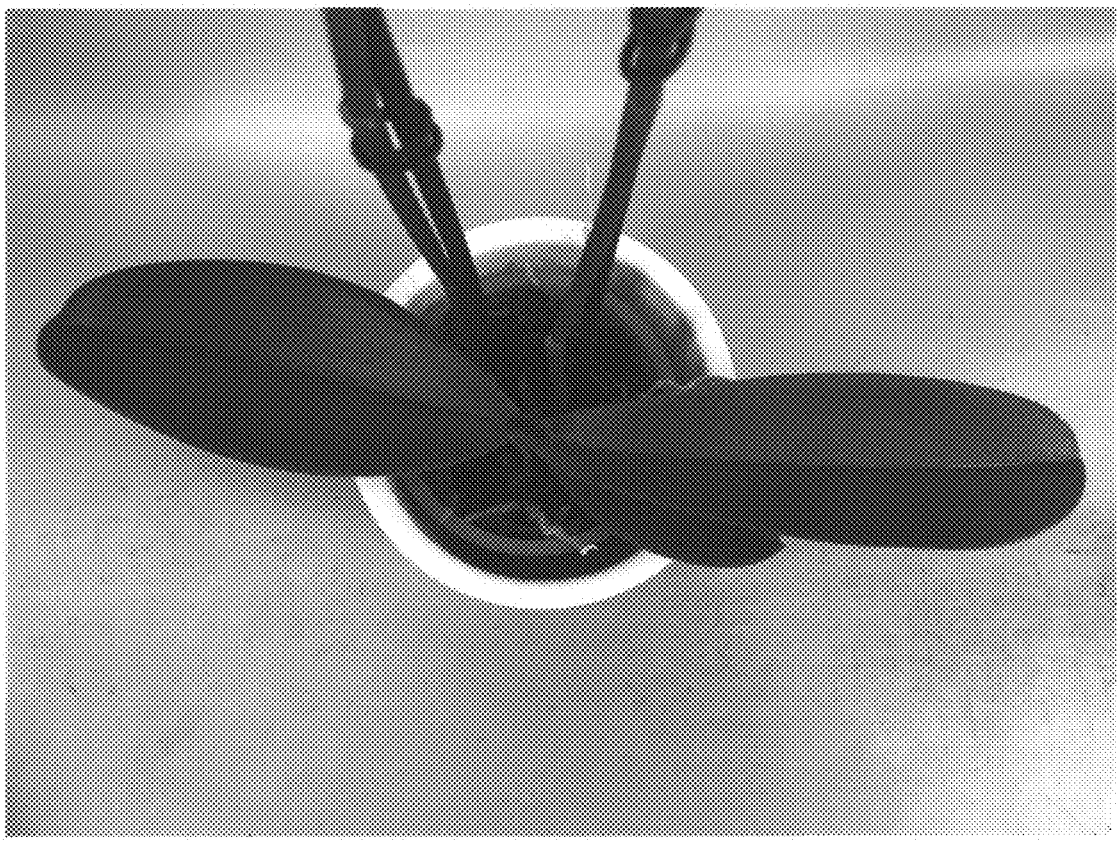
FIG. 3 shows an overhead view of the leaves of 'PHALHODIJ'.

The following detailed description sets forth the distinctive characteristics of 'PHALHODIJ'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in January 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALHODIJ'.

Parentage:

*Female parent*.—*Phalaenopsis* cultivar '27517-04' (unpatented).

*Male parent*.—*Phalaenopsis* cultivar '30031-01' (unpatented).

Propagation:

*Type*.—Meristem tissue culture.

Roots:

*Root description*.—Greyed-green (a color in between RHS 190B and RHS 190C) colored roots with branching lateral roots having yellowish-green (RHS N144A) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height* (*from soil level to top of inflorescence*).—Approximately 52.0 cm to 57.0 cm.

*Width* (*measured from leaf tips*).—About 34.0 cm to 36.0 cm.

*Vigor*.—Strong.

Leaves:

*Mature leaves*.—Quantity per plant: 7 to 8 leaves are produced before flowering. Length (fully expanded): 16.0 cm to 19.0 cm. Width: 6.0 cm to 7.0 cm. Position of the broadest part of the leaf: Toward the tip. Shape: Obovate. Base shape: Moderately elongated. Apex: Obtuse asymmetric. Leaf blade angle with the petiole (measured from the horizontal position): Between 10 degrees and 30 degrees. Leaf margin: Entire. Color: Upper surface: A color in between RHS 147A and RHS 146A. Lower surface: RHS 146B. Texture (both upper and lower surfaces): Smooth. Thickness: 2.0 mm to 3.0 mm. Variegation: Absent. Venation: Pattern: Parallel. Color of the midvein: Upper surface: RHS 147A. Lower surface: RHS 146B.

Peduncle:

*Quantity per plant*.—1 to 3.

*Number of flowers per peduncle*.—9 to 14.

*Length*.—52.0 cm to 57.0 cm.

*Diameter*.—4.0 mm to 5.0 mm.

*Strength*.—Strong.

*Aspect*.—Upright to slightly pendent.

*Texture*.—Smooth.

*Color*.—Green (RHS 146A).

*Internode length*.—3.5 cm to 4.5 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 3.

*Inflorescence size*.—Height (from base to tip): 200.0 mm to 250.0 mm.

*Flowering time*.—First flowers can be expected 10 to 11 months after planting in a 12-cm pot.

*Flower*.—Height: 78.0 mm to 83.0 mm. Diameter: 85.0 mm to 90.0 mm. Depth of lip: 18.0 mm to 20.0 mm.

*Flower longevity*.—On the plant: 14 to 17 weeks.

*Flower shape*.—Flat.

*Fragrance*.—Absent.

*Flower bud*.—Average size: Medium to large. Length: 21.0 mm to 23.0 mm. Width: 19.0 mm to 21.0 mm. Shape: Egg shaped. Color: Light green (a color in between RHS 145B and RHS 145C); purplish-red (RHS N77B) with a touch of (RHS N79B) toward the tip.

*Petals*.—Arrangement: Open/free. Shape: Semi-circular. Apex: Rounded to slightly mucronate asymmetric. Margin: Moderately undulated. Length (from base to tip): 40.0 mm to 42.0 mm. Width: 46.0 mm to 48.0 mm. Position of the broadest part of the petal: Toward the base. Color (when fully opened): Upper surface: Basic color: White (RHS NN155C). Over color: Reddish-purple shade (RHS N78B) at the base; dotted (RHS N78A). Lower surface: Basic color: White (RHS NN155C). Over color: Light purple (RHS N75B) at the base; light reddish-purple diluting dots (RHS N78D). Number of spots, dots, and stripes on the petals (upper surface): Many dots. Color of spots, dots, and stripes on the petals (upper surface): RHS N78A. Density of netting of the petals (upper surface): None. Color of the netting (upper surface): Not applicable.

*Dorsal sepal*.—Shape: Elliptic. Apex: Obtuse symmetric. Margin: Entire. Length (from base to tip): 44.0 mm to 46.0 mm. Width: 31.0 mm to 33.0 mm. Position of the broadest part of the dorsal sepal: Toward the base. Color (when fully opened): Upper surface: Basic color: White (RHS NN155C). Over color: Reddish-purple dots (RHS N78B). Lower surface: Basic color: White (RHS NN155C). Over color: Light purple (RHS 76A) with a touch of light yellow-green (RHS 145C). Number of spots, dots, and stripes on the dorsal sepals (upper surface): Very many dots. Color of spots, dots, and stripes on the dorsal sepals (upper surface): RHS N78B. Density of netting of the dorsal sepals (upper surface): None. Color of the netting: Not applicable.

*Lateral sepals*.—Shape: Broad ovate. Apex: Obtuse asymmetric. Margin: Entire; weakly twisted. Length (from base to tip): 39.0 mm to 41.0 mm. Width: 31.0 mm to 33.0 mm. Position of the broadest part of the lateral sepals: Toward the base. Color (when fully opened): Upper surface: Basic color: White (RHS NN155C). Over color: Touch of light yellow-green (RHS 145D) at the base; dotted (RHS N79C) at the middle and toward margin (RHS N78B). Lower surface: Basic color: White (RHS NN155C). Over color: Light yellow-green (a color in between RHS 145C and RHS 145D) at the middle from base toward tips; light purple (a color in between RHS 76A and RHS 76B) and diluting dots (RHS N78D). Number of spots, dots, and stripes on the lateral sepals (upper surface): Many to very many dots. Color of spots, dots, and stripes on the lateral sepals (upper surface): RHS N79C and RHS N78B. Density of netting of the lateral sepals (upper surface): None. Color of the netting (upper surface): Not applicable.

*Labellum* (*lip*).—Whiskers: Present. Length of whiskers: 16.0 mm to 18.0 mm. Color of whiskers: Touch of light purple (RHS 76A) at the base with light greenish-yellow tips (RHS 4C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Sinuated. Length: 19.0 mm to 21.0 mm. Width: 10.0 mm to 12.0 mm. Color: Upper surface: White (RHS NN155C) and striped (RHS 59B) at the base; reddish-orange (RHS 178C) toward margin on one side; reddish-purple (a color in between RHS N78B and RHS N78C) toward the other margin and tip. Lower surface: White (RHS NN155C); shaded (RHS 76A); reddish-orange (RHS 178D) toward margin on one side and purplish-pink margin (RHS N78C) toward other margin and tip. Number of spots and stripes on the lateral lobe: Few stripes. Color of spots and stripes on the lateral lobe: RHS 59B. Density of netting of the lateral lobe: None. Color of the netting: Not applicable.

*Apical lobe*.—Shape: Trullate; slightly folded upwards. Margin: Entire. Length: 19.0 mm to 21.0 mm. Width: 18.0 mm to 20.0 mm. Color: Upper surface: Dark purplish-pink (RHS 186C) at the base; reddish-orange wings (RHS 178C) and reddish-purple (RHS N78B) toward whiskers. Lower surface: White (RHS NN155B) at the middle from base toward whiskers; reddish-orange margins (RHS 178D) at wings; purplish-pink (RHS N78C) toward margins and whiskers. Number of spots and stripes on the apical lobe: None. Color of spots and stripes on the apical lobe: Not applicable. Density of netting of the apical lobe: None. Color of the netting: Not applicable.

*Callus*.—Average size: Small to medium. Height: 6.0 mm to 7.0 mm. Length: 6.0 mm to 7.0 mm. Width: 3.0 mm to 4.0 mm. Color: Yellowish-white (RHS 155B); dotted (a color in between RHS 59A and RHS 59B).

Reproductive organs:

*Column*.—Length: 8.0 mm to 10.0 mm. Diameter: 5.0 mm to 6.0 mm. Color: Touch of light reddish-purple (RHS N78D) at the base with white tip (RHS NN155C).

*Pollinia*.—Quantity: 2. Diameter: 0.8 mm to 1.0 mm. Color: Orange (RHS 25A).

*Ovary*.—Length: 14.0 mm to 16 0 mm. Diameter: 2.6 mm to 2.9 mm.

*Pedicel*.—Length: 40.0 mm to 42.0 mm. Diameter: 3.0 mm to 3.5 mm. Color: Yellow-green (a color in between RHS 144B and RHS 144C) at the base; light yellow-green (RHS 145C) and very light purple (RHS 76B) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALHODIJ' differs from the female parent plant '27517-04' (unpatented) in that 'PHALHODIJ' has apical lobes with a main color of reddish-purple and medium curvature of the lateral lobes, whereas '27517-04' has apical lobes with a main color of white and weak curvature of the lateral lobes.

'PHALHODIJ' differs from the male parent plant '30031-01' (unpatented) in that 'PHALHODIJ' has medium curvature of the lateral lobes, whereas '30031-01' has weak curvature of the lateral lobes. Additionally, 'PHALHODIJ' has larger flowers than '30031-01'.

'PHALHODIJ' is most similar to the commercial *Phalaenopsis* plants named 'PHALDOQZI' (U.S. Plant Pat. No. 30,031) and 'PHALFLACAN' (U.S. Plant Pat. No. 27,910). 'PHALHODIJ' differs from the commercial variety 'PHALDOQZI' in that 'PHALHODIJ' has trullate apical lobes, whereas 'PHALDOQZI' has triangular apical lobes. Additionally, 'PHALHODIJ' has smaller flowers and narrower petals than 'PHALDOQZI'.

'PHALHODIJ' differs from the commercial variety 'PHALFLACAN' in that 'PHALHODIJ' has trullate apical lobes and light purple whiskers at the base with light greenish-yellow tips, whereas 'PHALFLACAN' has rhombic apical lobes and dark purplish-red whiskers with light greenish-yellow tips.

I claim:

1. A new and distinct variety of *Phalaenopsis* plant named 'PHALHODIJ', substantially as described and illustrated herein.

* * * * *